(12) United States Patent
Yoneda et al.

(10) Patent No.: US 6,272,203 B1
(45) Date of Patent: Aug. 7, 2001

(54) X-RAY FLUORESCENCE INSPECTION APPARATUS

(75) Inventors: Eiji Yoneda, Naka-gun; Yasuhisa Asano, Kobe, both of (JP)

(73) Assignees: Mitsubishi Nuclear Fuel Co., Ltd., Naka-gun; Mitsubishi Heavy Industries, Ltd., Tokyo, both of (JP)

( * ) Notice: Subject to any disclaimer, the term of this patent is extended or adjusted under 35 U.S.C. 154(b) by 0 days.

(21) Appl. No.: 09/368,413

(22) Filed: Aug. 5, 1999

(30) Foreign Application Priority Data

Aug. 7, 1998 (JP) .................................................. 10-225021

(51) Int. Cl.[7] .................................................. G01N 23/223
(52) U.S. Cl. .................................................. 378/45; 378/44
(58) Field of Search .................................. 378/44, 45, 48, 378/49, 50

(56) References Cited

U.S. PATENT DOCUMENTS

| | | | |
|---|---|---|---|
| 5,103,470 | * 4/1992 | Iwamoto | 378/45 |
| 5,657,363 | * 8/1997 | Hossain et al. | 378/45 |
| 5,832,054 | * 11/1998 | Kuwabara | 378/45 |
| 5,898,752 | * 4/1999 | Van Der Wal | 378/49 |
| 5,982,847 | * 11/1999 | Nelson | 378/47 |
| 6,028,911 | * 2/2000 | Kawahara | 378/44 |

FOREIGN PATENT DOCUMENTS 6-18699   1/1994   (JP) .

* cited by examiner

*Primary Examiner*—David P. Porta
(74) *Attorney, Agent, or Firm*—Oblon, Spivak, McClelland, Maier & Neustadt, P.C.

(57) ABSTRACT

The apparatus enables measurement of the amount of contaminant in a welded portion to high accuracy and in a short time, using an X-ray fluorescence inspection apparatus. The end portion of a fuel rod having a bead portion on an end surface of an end plug is covered with an approximately cylindrical cap, with the bead portion exposed via a central aperture. The material of the cap is preferably titanium. With titanium the fluorescent X-ray radiation has a different wavelength from that of tungsten and zircaloy, and the amount of fluorescent X-ray radiation detected by a detector at a diffraction angle of the spectrum W-L α of fluorescent X-ray radiation for tungsten is less than those for tungsten and zircaloy. Therefore, while the fluorescent X-ray radiation of the cap which covers the end surface of the end plug around the bead portion results in noise, the amount of this fluorescent X-ray radiation measured by the detector is much smaller than for the tungsten and the zircaloy of the bead portion.

5 Claims, 11 Drawing Sheets

X-RAY FLUORESCENCE INSPECTION APPARATUS

BACKGROUND OF THE INVENTION

1. Field of the Invention

The present invention relates t o an X-ray fluorescence inspection apparatus which uses fluorescent X-rays to inspect the inclusion amount of a contaminant such as tungsten in a measurement portion of a material being inspected, such as in a pressure welded portion of a fuel rod for example.

2. Description of the Related Art

Heretofore, in the production of fuel rods for a nuclear fuel assembly for use in a light water nuclear reactor for example, as described in Japanese Patent Application, First Publication No. Hei-6-18699, a lower end plug is forced into one end of a cladding tube packed with a plurality of pellets, and a coil spring is then inserted from the other end and an upper end plug fitted, after which both ends are girth welded. An inert gas is then forced into the inside of the cladding tube via a seal aperture formed in a central region of the upper end plug, and the tube then sealed by pressure welding the seal aperture.

Figure 9:
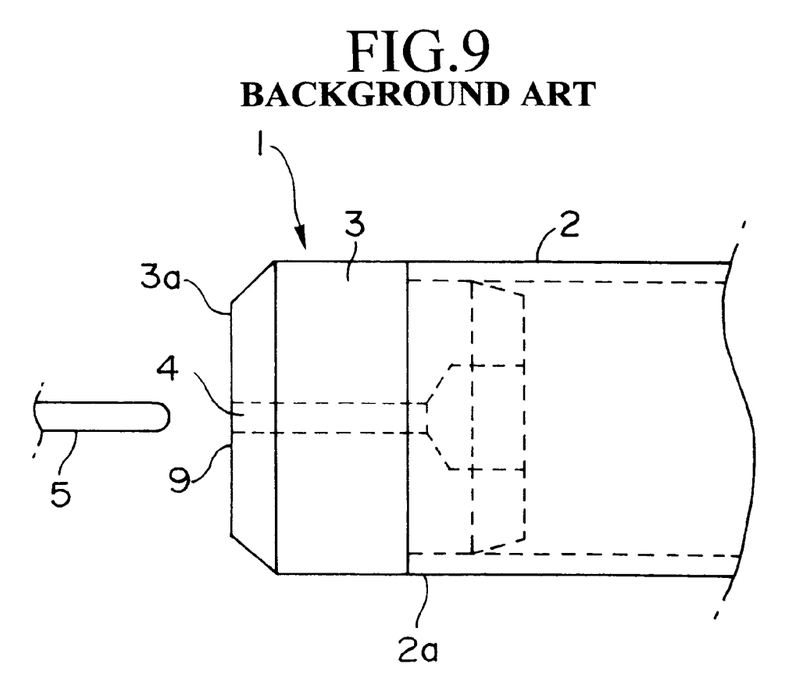
FIG. 9 is a diagram showing the pressure welding of a seal aperture of a fuel rod end plug.

For example in FIG. 9, which is a partial cross-sectional view showing the upper end plug fitted into the cladding tube, the pressure welding is conducted inside a sealed chamber. That is, an end portion 2a of a cladding tube 2 of a fuel rod 1 is positioned inside a chamber (not shown in the figure), and an upper end plug 3 is then forced into the end portion 2a of the cladding tube and girth welded. The upper end plug 3 incorporates a seal aperture 4 which passes through a central portion of an end surface 3a of the end plug 3.

Figure 10:
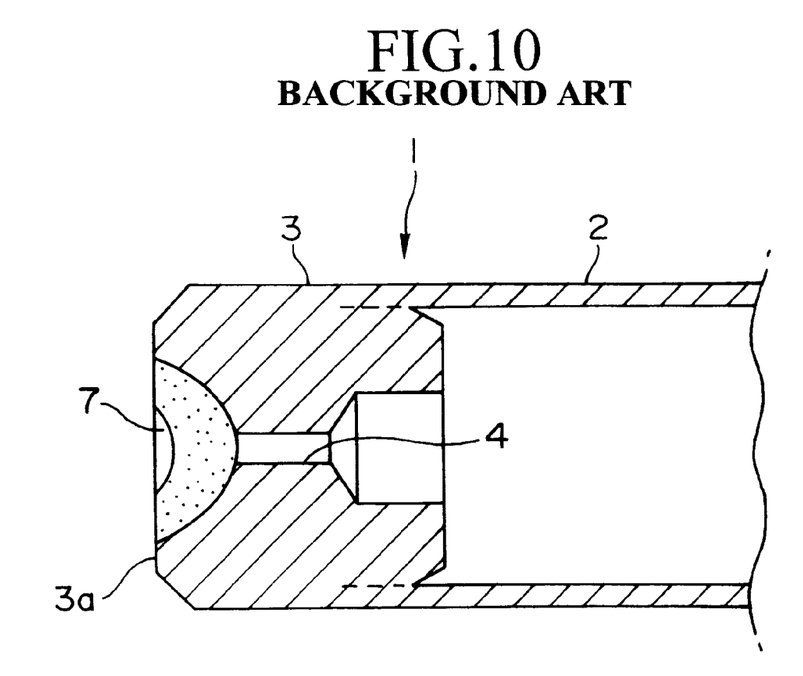
FIG. 10 is a longitudinal cross-sectional diagram showing a bead portion following the pressure welding of a seal aperture of a fuel rod end plug.

Then an inert gas such as helium is forced in through the seal aperture 4, and with the system under pressure, arc welding from a tungsten electrode 5 is then used to seal weld the seal aperture 4. The arc discharge causes the periphery of the seal aperture 4 of the end plug 3 to melt, thus seal welding the aperture 4 shut. Following completion of the welding of the aperture 4, then as shown in FIG. 10 a bead portion 7 (welded portion) is produced in the center of the end surface 3a by pressure welding.

However, since for reasons of corrosion resistance and neutron economy, the end plug 3 of the fuel rod 1 is made of zircaloy, then when the seal aperture 4 of the end plug 3 is pressure welded using a tungsten electrode 5, because a large voltage is applied, a phenomenon can occur where the tungsten of the tungsten electrode 5 melts and is splashed into and mixed with the melted bead portion 7 of the end plug 3. This is known as tungsten inclusion. Mixing of tungsten with the zircaloy of the end plug 3 is undesirable as it causes a deterioration in the corrosion resistance of the end plug 3.

Consequently, heretofore the end plugs 3 of fuel rods 1 are inspected for tungsten inclusions, and defective end plugs with a large amounts of inclusions and poor corrosion resistance are detected.

Examples of inspection apparatus for inspecting the amount of tungsten inclusions include apparatus based on X-ray through transmission methods. With this inspection method X-rays are irradiated from an X-ray generation apparatus, and are transmitted through the end plug 3 to produce an X-ray projection on a film. In those cases where there are tungsten inclusions within the bead portion 7 of the end plug 3, because the tungsten is almost impenetrable to X-rays, white portions appear on the image, enabling detection of the tungsten inclusions as well as a determination of the amount of inclusions.

However, this inspection method requires the developing of a film, which can take time. Moreover the tungsten is detected by an examiner viewing the film, which requires experienced personnel.

X-ray fluorescence inspection apparatus have been proposed as inspection apparatus which can help overcome the above problems. These X-ray fluorescence inspection apparatus include both large scale stationary apparatus a s well as small scale portable types.

The large stationary types of apparatus use a method whereby X-rays are irradiated down on to the material being inspected, the X-ray output being large and the precision high. However, whereas the bead portion 7 being inspected is of an approximate diameter of 3 mm, the fuel rod 1 is a cylinder of total length 4 m and diameter 10 mm. In order to inspect a plurality of this type of fuel rod 1 on line, it is preferable if the fuel rods 1 are arranged horizontally with the X-rays being irradiated in a horizontal direction. This orientation however is not possible with a large stationary X-ray fluorescence inspection apparatus.

Figure 11:
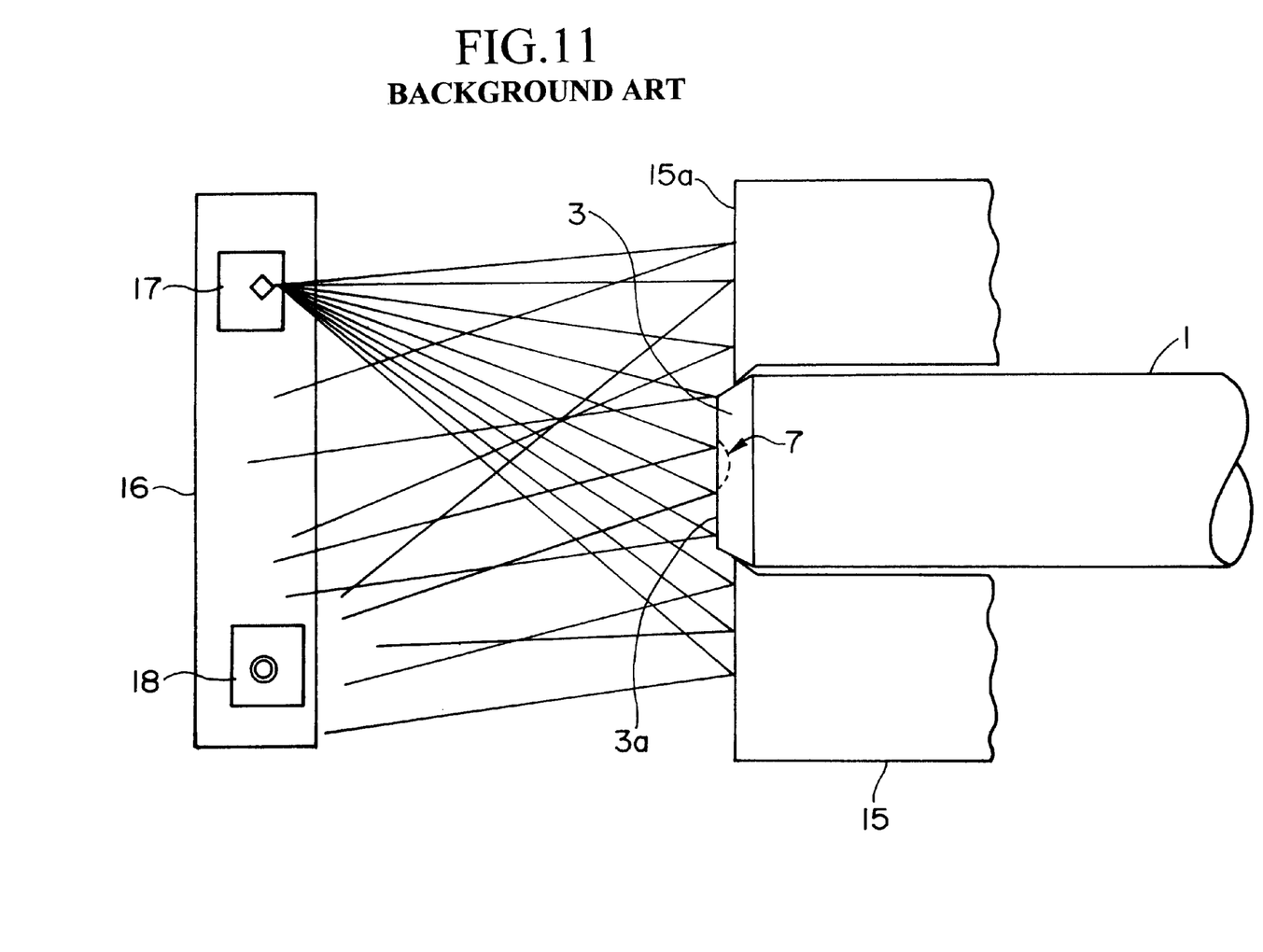
FIG. 11 is a diagram showing a conventional X-ray fluorescence inspection apparatus for measuring the amount of tungsten inclusions.

On the other hand, with the portable types of X-ray fluorescence inspection apparatus, horizontal al irradiation of the X-rays is possible, as shown in FIG. 11 for example.

With the X-ray fluorescence inspection apparatus shown in FIG. 11, a holder 15 constructed of steel or the like, is mounted around the circumference of the end plug 3 of the fuel rod 1, with a surface 15a of the holder 15 approximately parallel with the end surface 3a of the end plug 3. A portable X-ray fluorescence inspection device 16 is then positioned facing the end surface 3a of the end plug 3.

The portable X-ray fluorescence inspection device 16 irradiates primary X-rays from an X-ray tube 17 in an approximately horizontal direction toward the bead portion 7 of the end surface 3a. A fluorescent X-ray detection apparatus 18 then detects and measures fluorescent secondary X-rays generated at the end surface 3a of the bead portion 7.

The measurement principles relating to this type of X-ray fluorescence inspection device 16 will now be explained with reference to FIG. 12.

Primary X-rays are irradiated from the X-ray tube 17 at the bead portion 7 of the end surface 3a of the end plug 3, exciting elements included within the bead portion 7. The excited elements then produce fluorescent X-rays of a specific wavelength in the form of secondary X-rays. The fluorescent X-rays pass through a divergence slit 19 in the detection apparatus 18 and are directed at an analyzing crystal 20 where e diffraction into an X-ray spectrum occurs for each wavelength, at an angle θ determined by the Bragg formula shown below.

$$n\lambda = 2d \sin \theta$$

where n is the degree (n=1,2,3 ... ), λ is the wavelength (Å), d is the spacing of the lattice planes of the crystal, and θ is the diffraction angle (°)

Then, each fluorescent X-ray spectrum passes through a light intercepting slit 21 and is detected by a detector 22 and measured.

Figure 12:
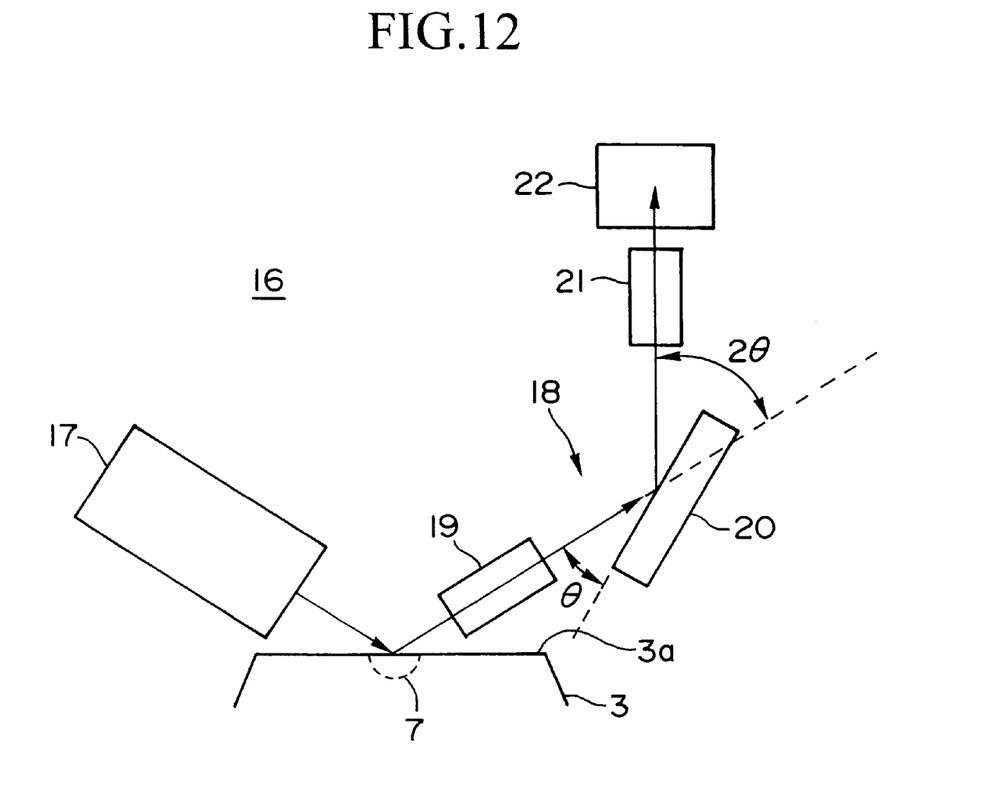
FIG. 12 is a schematic representation of the construction of an X-ray fluorescence inspection apparatus.

The analyzing crystal 20, the detector 22 and the light intercepting slit 21 are configured as shown in FIG. 12 to enable scanning to be conducted while maintaining the double angle relationship (θ-2θ) with respect to the fluorescent X-rays being irradiated on to the analyzing crystal 20. Consequently by scanning the analyzing crystal 20, the detector 22 and the light intercepting slit 21 across the entire angle range (13°~98°), the fluorescent X-rays of specific elements can be detected at specific angles (wavelengths). The fluorescent X-rays detected are converted to a voltage pulse by the detector 22 and are then sent to either a scaler (scaling circuit) or a rate meter, which are not shown in the diagram, and the X-ray intensity then displayed as a coefficient.

The wavelength of the fluorescent X-ray is specific for each element and can be used for identification of element s such as tungsten. The X-ray intensity at each wavelength is proportional to the amount of that element contained in the sample material.

The portable X-ray fluorescence inspection device 16 however does not provide an apparatus for the simple adjustment of the primary X-ray irradiation range (the measurement range), and because the X-ray beam diffuses in the direction of the irradiation, using a stainless steel holder 15 as a positioning jig will generate unwanted fluorescent X-rays from the holder 15 which will appear as noise at the detection apparatus 18 resulting in a lowering of the accuracy of the inspection.

Furthermore, the fluorescent X-ray spectra Zr-Kα, Zr-Kβ resulting from excitation of the zircaloy of that portion of the end surface 3a of the end plug 3 surrounding the bead portion 7 is also detected by the detection apparatus 18, and because a multiple of the wavelength of the spectra Zr-Kα, Zr-Kβ is very similar to the wavelength of the fluorescent X-ray spectrum for tungsten W-Lα, the spectra Zr-Kα, Zr-Kβ are detected by the detector 22 as noise together with the tungsten fluorescent X-rays, and as the amount of noise is considerable an accurate determination of the amount of tungsten inclusion cannot be made. Furthermore, although measurement over an extended time period produces an improvement in the accuracy of the inspection, this results in a deleterious reduction in the productivity of the inspection.

Moreover, in the case of fuel rods with differing external dimensions, even if the various beads 7 contain the same proportion of tungsten, because the dimensions, shape and surface area of the end surfaces 3a of the end plugs 3 will be different, the amount of fluorescent X-ray radiation detected by the detector 22 will also be different, and so the measured values of the fluorescent X-rays detected will differ. Consequently, the complication arises that a different calibration curve (inspections standard) needs to be provided for each type of fuel rod 1 in order to determine whether or not the product is of an acceptable standard.

SUMMARY OF THE INVENTION

The present invention takes the above problems into consideration, with the object of providing an X-ray fluorescence inspection apparatus which is capable of highly accurate measurements by eliminating to a large extent the amount of noise resulting from fluorescent X-ray radiation generated from components other than the portion being measured.

The X-ray fluorescence inspection apparatus according to the present invention comprises: an X-ray generator for irradiating the portion of the sample with primary X-rays; a fluorescence X-ray detecting device for detecting fluorescence X-rays generated by the portion of the sample; and a shielding member for shielding a peripheral region of the sample which surrounds the portion of the sample; the shielding member having an opening corresponding to the portion to be inspected, and the shielding member being constructed of a material for which the wavelength of fluorescent X-rays is different from the wavelength of fluorescent X-rays from the contaminant and the sample and for which the intensity of fluorescent X-rays at the diffraction angle of the contaminant is less than the intensity of each of the fluorescent X-rays from both the contaminant and the sample.

Fluorescent X-rays generated by excitation of elements in the material surrounding the portion being inspected will enter the fluorescence X-ray detecting device and appear as noise. However by covering the area surrounding the portion to be inspected with the shielding member, the wavelength of fluorescent X-ray radiation resulting from excitation within the shielding member, as measured by the X-ray fluorescence inspection apparatus, will differ from the wavelength of fluorescent X-ray radiation from the portion to be inspected, and provided measurements are conducted at the diffraction angle corresponding to the fluorescent X-rays generated by excitation of the contaminant in the portion, the amount of noise is reduced as much as possible. Moreover, the amount of fluorescent X-ray radiation resulting from the contaminant will be significantly larger than the amount of noise, enabling an accurate measurement to be conducted in a very short time.

The sample may be a fuel rod comprising an end plug at one end thereof, the portion to be inspected may be a welded portion formed on the center of the end plug. In this case, the shielding member may comprise a cylindrical body in which the one end of the fuel rod can be accommodated and a base plate closing one end of the cylindrical body, and an aperture may be formed at the center of the base plate. Furthermore, the shielding member may be formed of titanium or iron.

The X-ray fluorescence inspection apparatus may further comprises a longitudinal positioning device for determining the position of the fuel rod in a longitudinal direction of the fuel rod, and a radial positioning device for determining the position of the fuel rod in a radial direction of the fuel rod.

A plurality of shielding members having the same external dimensions may be used for covering a plurality of samples even if the external dimensions of the samples should differ. By making uniform the shape of the shielding members, even if the external dimensions of the samples to be inspected should differ, because the fluorescent X-ray noise generated by excitation within the area surrounding the aperture will not only be minimal, but also uniform, the background value arising from noise and the like will not vary. Hence the same calibration curve can be used to determine the acceptability of the sample even if the external dimensions of the samples to be inspected should differ.

Furthermore, the welded portion can also be a pressure welded portion which includes tungsten as a contaminant. When arc discharge from a tungsten electrode is used to pressure weld a pressure weld portion, even if some tungsten is included in the pressure welded portion, fluorescent X-ray inspection can still be used to detect tungsten inclusions, and by using a calibration curve, determine acceptability.

DESCRIPTION OF THE PREFERRED EMBODIMENT

Figure 1:
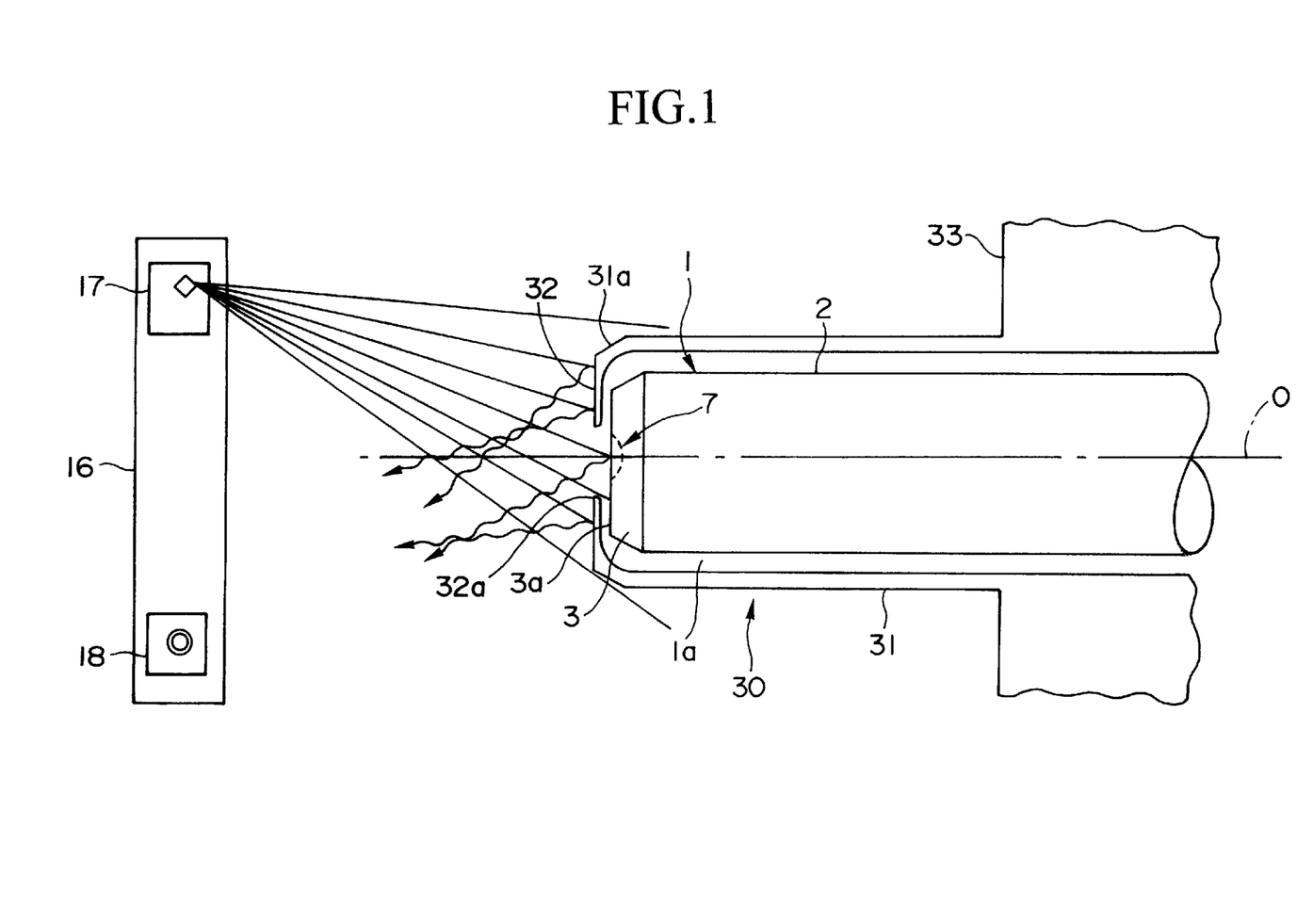
FIG. 1 is a diagram showing the essential components of an inspection apparatus according to an embodiment of the present invention for inspection of a bead portion of a fuel rod end plug using fluorescent X-ray radiation.
Figure 2:
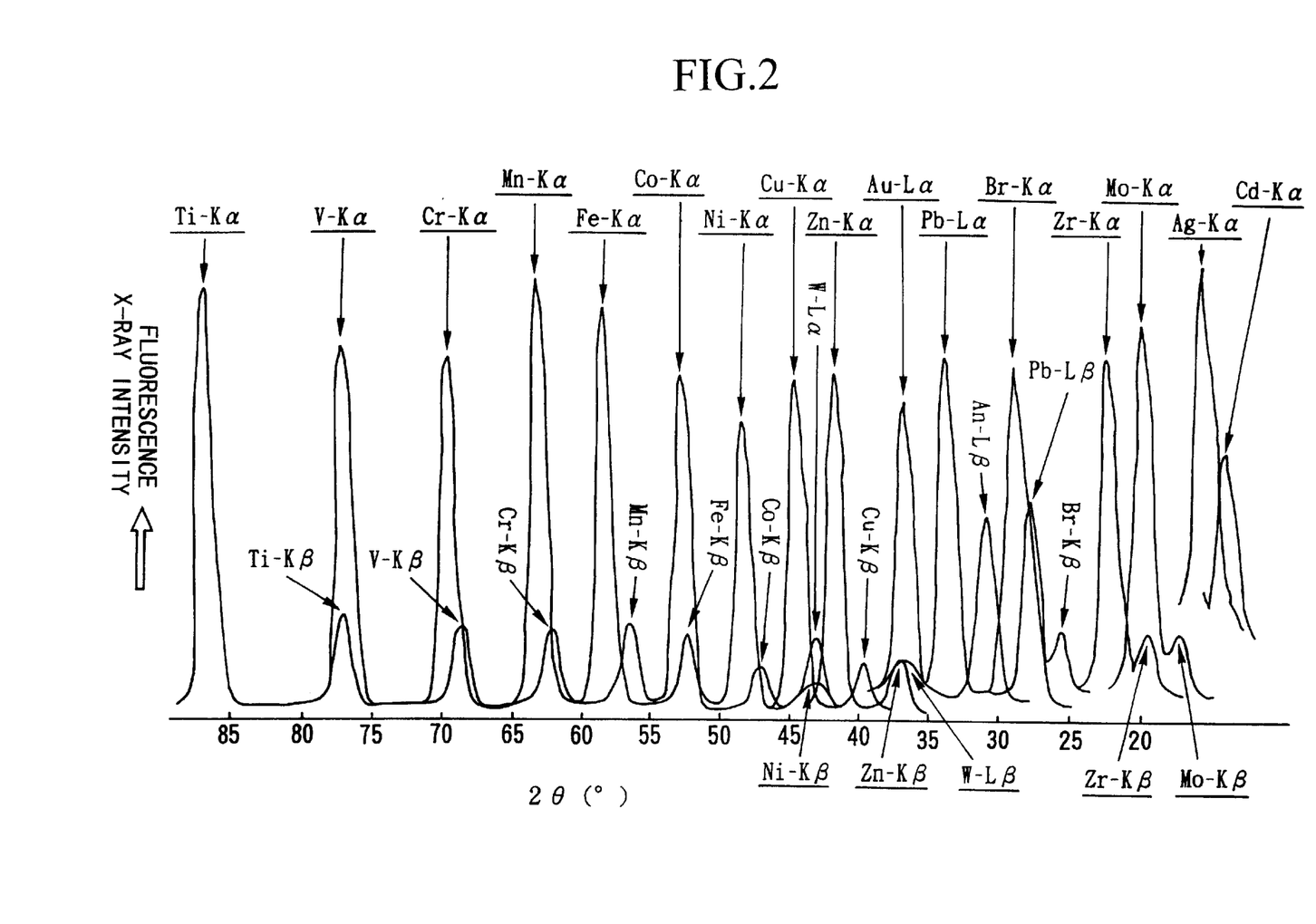
FIG. 2 is a diagram showing fluorescent X-ray spectral profiles and overlaps.
Figure 3:
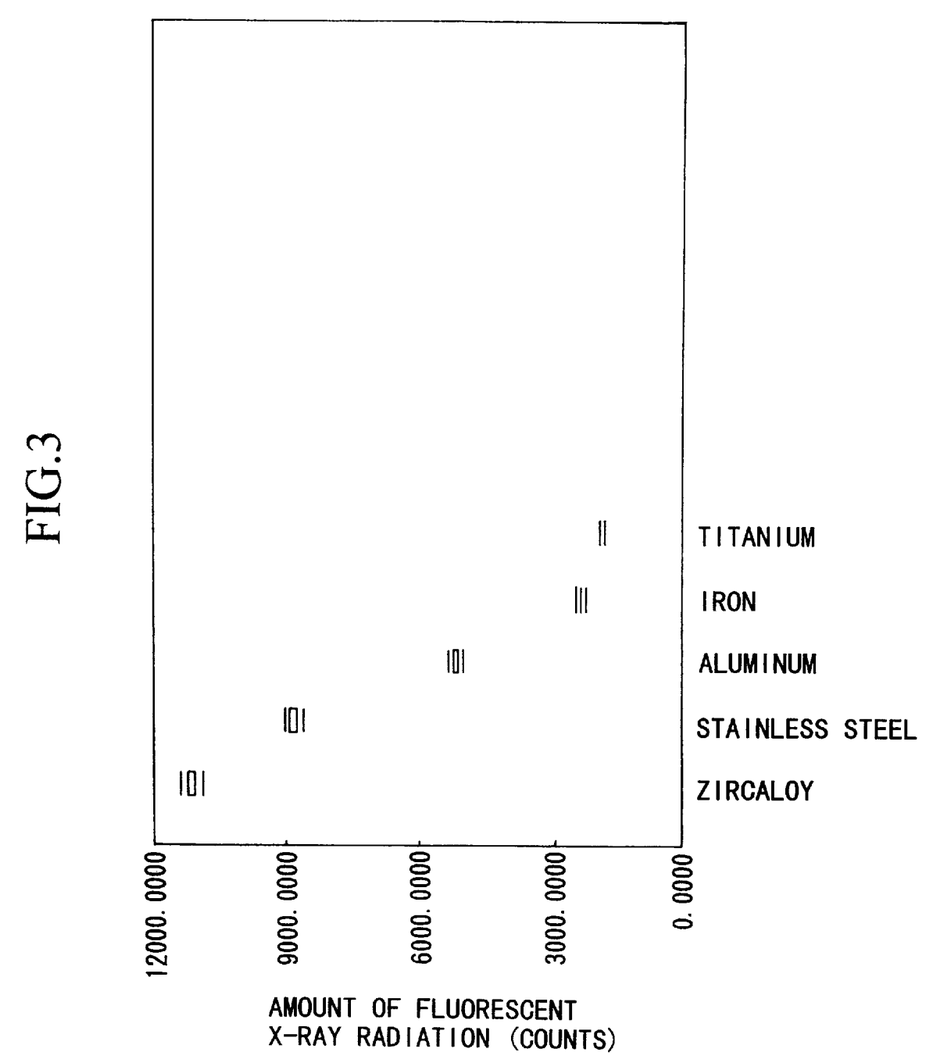
FIG. 3 is a graph showing the amount of fluorescent X-ray radiation for zircaloy and various cap materials.
Figure 4:
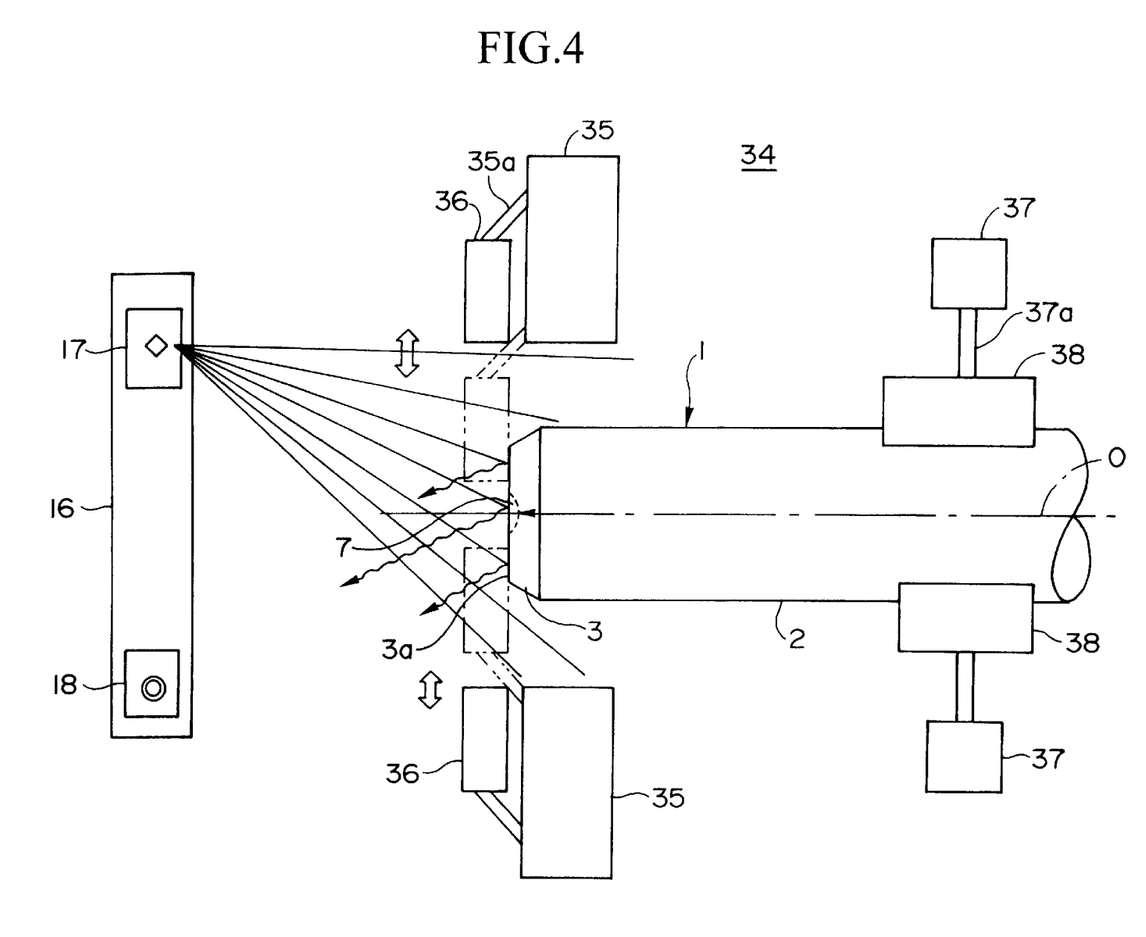
FIG. 4 is a diagram showing a fuel rod positioning apparatus during an inspection by an X-ray fluorescence inspection apparatus according to an embodiment of the present invention.
Figure 5:
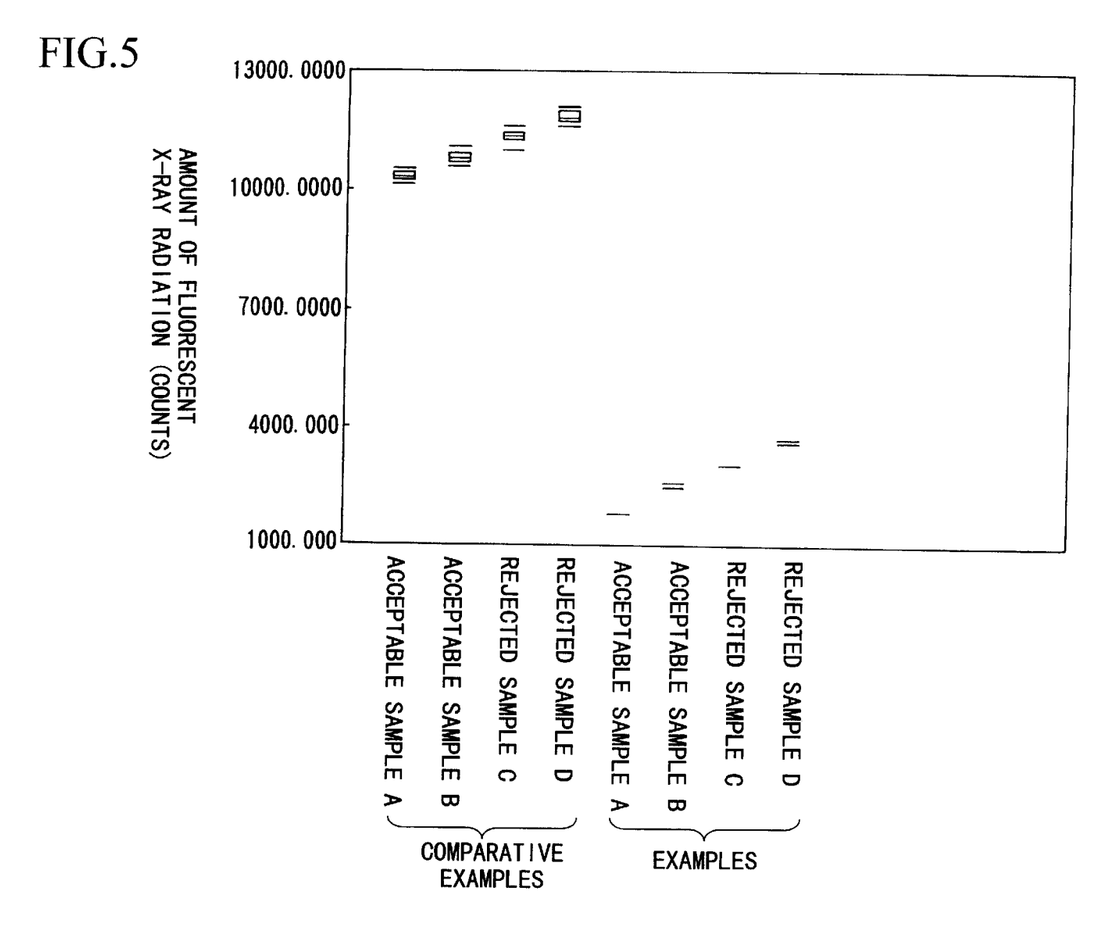
FIG. 5 is a graph showing the results of fluorescent X-ray inspection on samples using both an embodiment of the present invention and a conventional technology apparatus.

An embodiment of the present invention is described below with reference to the FIG. 1 through FIG. 5. For those portions which are the same as those described in the conventional technology above, the same numerals are used and the explanation thereof is incorporated herein. FIG. 1 is a diagram showing the essential components of the end portion of a fuel rod, and an X-ray fluorescence inspection apparatus according to an embodiment of the present invention. FIG. 2 is a diagram showing the fluorescent X-ray spectral profiles and overlaps for the various metals in terms of the relationship between the diffraction angle $2\alpha$ which corresponds to the wavelength of the specific metal, and the fluorescent X-ray intensity. FIG. 3 is a graph showing the amount of fluorescent X-ray radiation for a group of metals measured at a diffraction angle corresponding to the wavelength of the fluorescent X-ray spectrum W-L$\beta$. FIG. 4 is a diagram showing the positioning of an end plug of a fuel rod prior to inspection. FIG. 5 is a graph showing the amounts of fluorescent X-ray radiation measured for a sample of the present embodiment which uses a cap, and a sample according to conventional techniques in which no cap was used.

With the X-ray fluorescence inspection apparatus 15 of FIG. 1, an upper end plug (hereafter referred to as the end plug) 3 is forced into one end of a cladding tube 2 of a fuel rod 1 which is being inspected, and then girth welded. A seal aperture 4 is then pressure welded using the conventional techniques described above. An X-ray fluorescence inspection device 16 is positioned facing the end surface 3a of the end plug 3. The X-ray fluorescence inspection device 16 incorporates the construction as shown in FIG. 12.

The end portion of the fuel rod 1 is covered with an approximately cylindrical cap 30 open at one end and formed with a base (front end). At the front end of a cylindrical main body 31 of the cap 30 is provided a front surface 32 which is equipped with an opening such as a circular central aperture 32a so that the end surface 3a of the end plug 3 is covered, while the bead portion 7 is exposed. The central aperture 32a is of the same diameter (for example, approximately 3 mm) as the external diameter of the bead 7 of the end plug 3, or can also be slightly larger.

Moreover, the external dimensions of the fuel rod 1 will vary depending on the type of rod. Therefore a variety of caps 30 are formed so that the internal dimensions thereof are appropriate for the external dimensions of the various types of fuel rod 1, and the external dimensions thereof will be the same and will give the same shape regardless of any variation in the type of fuel rod 1. As a result, when the cap 30 is used to cover the end portion of the fuel rod 1, even if there is a slight variation in the external shape of the fuel rod 1 due to the type of rod being used, since the entire bead portion 7 is exposed to the outside through the central aperture 32a, the external shape of the main body 31 and the front surface 32 remains the same.

The connection portion between the front surface 32 and the main body 31 of the cap 30 comprises a beveled surface 31a around the circumference of the cap so that the cap has an approximately uniform thickness. Moreover, at a position on the outer surface of the main body 31 some distance away from the front surface 32 in the direction of the axis O of the fuel rod 1, an expanded diameter portion (flange) 33 is formed to protrude from the outer surface of the main body 31.

Because the cap 30 is used during inspection of the amount of tungsten en inclusions in the bead portion 7 that comprises the welded portion of the fuel rod 1 being inspected, the material for the cap 30 should preferably be a metal for which excitation generates fluorescent X-rays of a wavelength different from the wavelengths of the fluorescent X-rays generated by excitation of the zircaloy and the tungsten inclusions which comprise the bead portion 7, and moreover for which the amount of fluorescent X-ray radiation measured at the diffraction angle corresponding to the wavelength of the tungsten spectrum W-L$\alpha$ shown in FIG. 2 is less than amount of fluorescent X-ray radiation measured for either the tungsten or the zircaloy. A suitable example is titanium as shown in FIG. 3. In this way it is possible to reduce the amount of noise fluorescent X-ray radiation during measurement by the detection apparatus 18, thus enabling a simple and accurate determination of the amount of fluorescent X-ray radiation being generated by the tungsten.

FIG. 2 shows the spectral profiles and overlaps for fluorescent X-ray radiation generated by excitation of various metals, with the horizontal axis representing the diffraction angle $2\theta$ for the analyzing crystal 20 in the detection apparatus 18 which corresponds with the wavelengths of the various fluorescent X-rays. The vertical axis represents the intensity of the fluorescent X-rays. In the figure the spectrum W-L$\beta$ for fluorescent X-rays generated from tungsten overlaps with Zn-K$\beta$ in terms of both intensity and angle, whereas the spectrum W-L$\alpha$ does not overlap with any other fluorescent X-ray radiation in terms of intensity. It is therefore preferable to use the spectrum W-L$\alpha$ for detecting the presence of tungsten.

The diffraction angle of the fluorescent X-ray spectrum Ti-K$\alpha$ for titanium (approximately 86°) is far removed from that of the tungsten spectrum W-L$\alpha$ ($2\theta \approx 43°$) However, the diffraction angles $2\theta$ of the fluorescent X-ray spectra Zr-K$\alpha$, Zr-K$\alpha$ for zirconium alloy are approximately 23° and 19° respectively, and because multiples of these values are positioned close to the diffraction angle of the spectrum W-L$\alpha$, these spectra can easily be mistaken for the spectrum W-L$\alpha$.

FIG. 3 shows the experimental results for the amount of fluorescent X-ray radiation measured for a group of metals at a diffraction angle 2θ (≈43°) corresponding to the wavelength of the fluorescent X-ray spectrum W-Lα of tungsten.

The samples used for the experiment were 50×50 mm plates of 100% pure zircaloy, stainless steel, aluminum, iron, and titanium respectively.

Each sample was set in a position corresponding to the bead portion 7 of the end plug 3 facing the X-ray fluorescence inspection device 16 of the X-ray fluorescence inspection apparatus, and then irradiated with primary X-rays and the amount of fluorescent X-ray radiation generated through excitation within the sample measured for a period of ten seconds. Each sample was measured ten times, with the results being shown in FIG. 3.

As can be seen from the measurement results in FIG. 3, because multiples of the diffraction angle (wavelength) for the zirconium alloy are close to the diffraction angle of tungsten, both the amount of fluorescent X-ray radiation measured and the variation between individual measurement values was the largest observed. Furthermore, following the zirconium alloy, stainless steel and aluminum were the next largest in terms of the amount of fluorescent X-ray radiation measured. Although not shown in the figure, the amount of fluorescent X-ray radiation for tungsten would be more than ten times that shown for the zircaloy.

In contrast, the titanium displayed the smallest amount of fluorescent X-ray radiation, and the variation between individual measurement values was also small. The next most preferred metal would be iron. By using either of these two metals, the amount of noise during measurement of the amount of tungsten fluorescent X-ray radiation can be reliably reduced.

The results of these experiments suggest titanium will be most preferable as the material for the cap, with iron being the next most favorable. However because iron will rust it is not considered suitable.

The X-ray fluorescence inspection apparatus is equipped with a positioning device 34 as shown in FIG. 4, which can be moved in and out for positioning the end portion of the fuel rod 1 in a position facing the X-ray fluorescence inspection device 16. The positioning device 34 is equipped with positioning members 36 which are each connected to a first cylinder 35 via an arm 35a. The end surface 3a of the end plug 3 of the fuel rod 1 contacts the positioning members 36 at the positioning location thus positioning the fuel rod.

Furthermore, the positioning device 34 is also equipped with a second cylinder 37 for gripping the external surface of the fuel rod 1 and moving the rod into position. A holding portion 38 which is connected via an arm 37a grips and moves the fuel rod 1.

The X-ray fluorescence inspection apparatus 15 according to the embodiment of the present invention is constructed as detailed above. As follows is an explanation of a method for inspecting the amount of tungsten inclusions using the X-ray fluorescence inspection apparatus 15.

First, the first cylinders 35 are used to move the positioning members 36 into the positions required for fluorescent X-ray inspection, indicated by the dashed lines in FIG. 4. A fuel rod 1 in which the end plug 3 and the cladding tube 2 have been welded is then gripped by the holding portions 38 of the second cylinders 37 and moved in a direction along the axis O of the fuel rod 1 to the position where it contacts the positioning members 36. This completes the positioning of the fuel rod 1. Next, the positioning members 36 of the first cylinders 35 are moved radially back and away from the fuel rod 1 and returned to the initial positions, distant from the point of the primary X-ray irradiation.

The front end of the fuel rod is then covered with the cap 30, which is positioned so that the central aperture 32a in the front surface 32 of the cap 30 lines up with the bead portion 7 on the end surface 3a of the end plug 3. In this position, because the expanded diameter portion 33 of the cap 30 is located in front of the second cylinders 37, the external surface of the fuel rod 1 will not be irradiated by the primary X-rays from the X-ray tube 17 of the inspection device 16.

If the X-ray fluorescence inspection device 16 is activated under these conditions, then as shown in FIG. 1, primary X-rays will be emitted from the X-ray tube 17 and irradiate the front surface 32 of the cap 30, as well as passing through the central aperture 32a and irradiating the bead portion 7. Fluorescent X-rays generated by excitation of the bead portion 7 and the front surface 32 of the cap 30 then enter the detection apparatus 18. Fluorescent X-rays generated by irradiation of other portions of the apparatus with primary X-rays proceed in different directions and will not enter the detection apparatus 18.

With the detection apparatus 18, those fluorescent X-rays which pass through the divergence slit 19 are diffracted by the analyzing crystal 20 which is set at a predetermined angle θ corresponding to the fluorescent X-rays being inspected, and the diffracted fluorescent X-rays which have an angle of 2θ relative to the fluorescent X-rays prior to diffraction, then pass through the light intercepting slit 21 and are detected by the detector 22 and the amount of fluorescent X-ray radiation then measured. In this case, the analyzing crystal 20, the light intercepting slit 21 and the detector 22 are set for a θ:2θ relationship with respect to the fluorescent X-ray radiation which passes through the divergence slit 19. Moreover the diffracted fluorescent X-rays are measured by the detector 22 at an angle equivalent to the diffraction angle 2θ (≈43°) of the spectrum W-Lα.

Consequently, the fluorescent X-rays generated by excitation of the front surface 32 of the cap 30, and the bead portion 7 are detected and measured by the detector 22 at the diffraction angle 2α of the spectrum W-Lα.

With this embodiment, because fluorescent X-rays of a diffraction angle of the spectrum W-Lα are being detected by the detector 22, then of the measured fluorescent X-rays, the amount of noise due to titanium fluorescent X-rays, generated by excitation of the front surface 32 of the cap 30, is extremely small, and fluorescent X-ray radiation which was not generated from the bead portion 7 can be kept to an absolute minimum.

As a result, the amount of fluorescent X-ray radiation from the zircaloy of the bead portion 7, and the amount of fluorescent X-ray radiation from tungsten inclusions within the bead portion 7 is relatively high. The fluorescent X-ray radiation from the zircaloy is noise, and because a multiple of the diffraction angle 2θ thereof is quite similar to the diffraction angle for W-Lα, the amount of zircaloy fluorescent X-ray radiation detected is high. However, because the amount of fluorescent X-ray radiation of the spectrum W-Lα, which is the object of the inspection, is approximately ten times the amount of zircaloy fluorescent X-ray radiation, the amount of tungsten included in the bead portion 7 can be determined quickly and reliably, and highly accurate measurements are possible.

A series of experiments was conducted relating to the amount of tungsten inclusions in the bead portion 7 of an end plug 3, by measuring the amount of fluorescent X-ray radiation from four fuel rods A, B, C, D, using both the embodiment of the present invention which utilizes a cap, as well as a conventional apparatus with no cap. The results are shown in FIG. 5.

In the case of the present embodiment, because the area surrounding the bead portion 7 is covered by the titanium of the end surface 32 of the cap 30, the amount of fluorescent X-ray radiation at the diffraction angle of the spectrum W-Lα is extremely small, while the amount of fluorescent X-ray radiation from the tungsten and zircaloy of the bead portion 7 is large. Hence, determination of the amount of tungsten fluorescent X-ray radiation is simple, and the amount of fluorescent X-ray radiation (the count) detected by the detector 22 for each of the samples A, B, C, D is small.

Moreover, ten separate measurements were conducted for each sample, and samples A, B, C and D showed no overlap in terms of the fluorescent X-ray count, and also displayed little variation between measurements, enabling a precise measurement to be made.

As a result of the measurements and based on a pre-set calibration curve, samples A and B were deemed to have passed, and samples C and D to have failed.

In contrast, with the conventional technology example, fluorescent X-ray radiation of the spectra Zr-Kα, Zr-Kβ generated by excitation of the zirconium alloy surrounding the bead portion 7 of the end surface 3a of the end plug 3 is measured as noise, and because the amount of this type of fluorescent X-ray radiation is large, the overall amount of fluorescent X-ray radiation detected for the samples A, B, C, and D was higher than for the embodiment of the present invention. Moreover, the measured values were inaccurate with a large variation in the data for the ten separate measurements and some overlap in the values for the various samples A, B, C, and D. With the conventional technology example the amount of noise is large making the measurement inaccurate, and consequently in order to improve the accuracy, measurements would need to be conducted over a longer time period.

Figure 6:
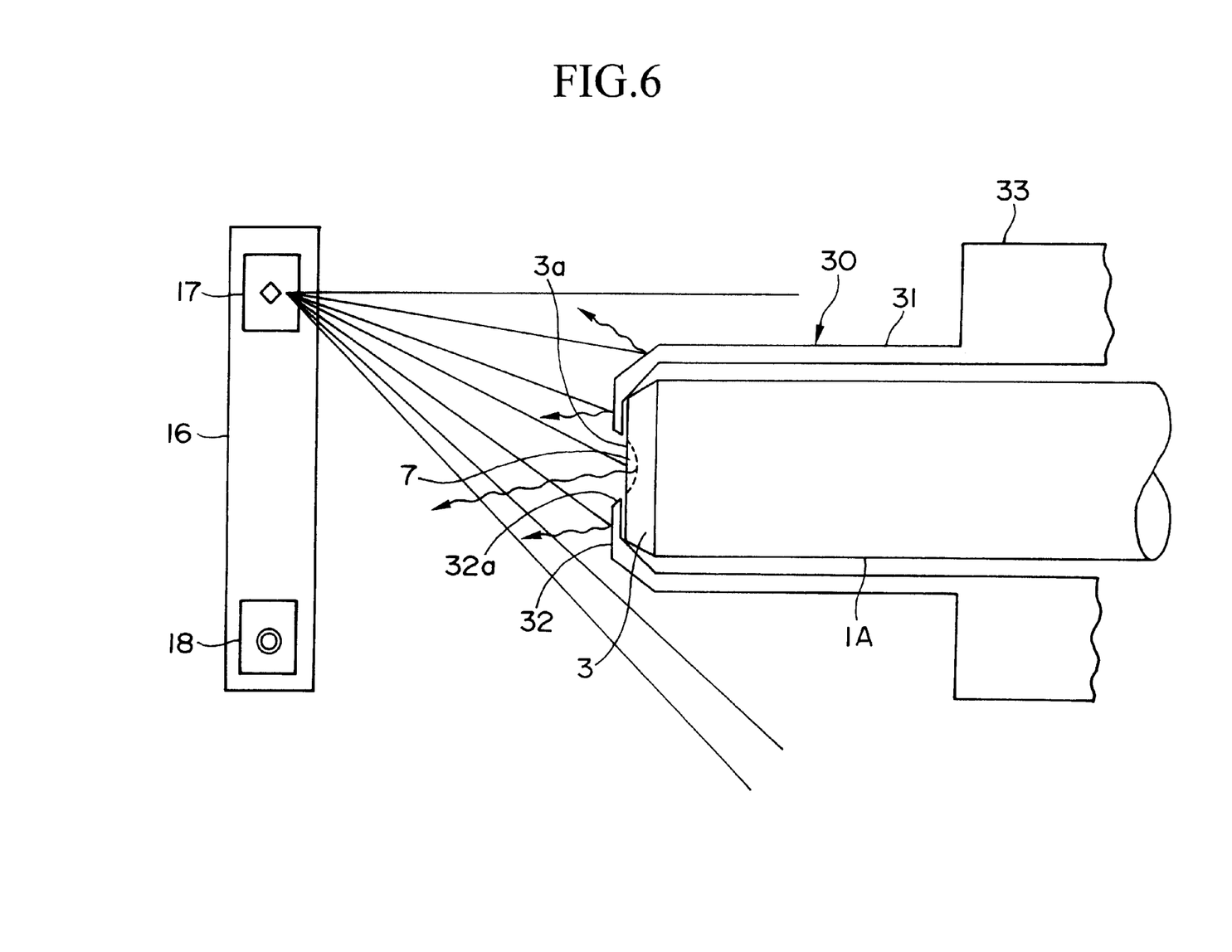
FIG. 6 is a diagram showing a fluorescent X-ray inspection of a fuel rod of a shape different from that of the embodiment of the present invention.
Figure 7:
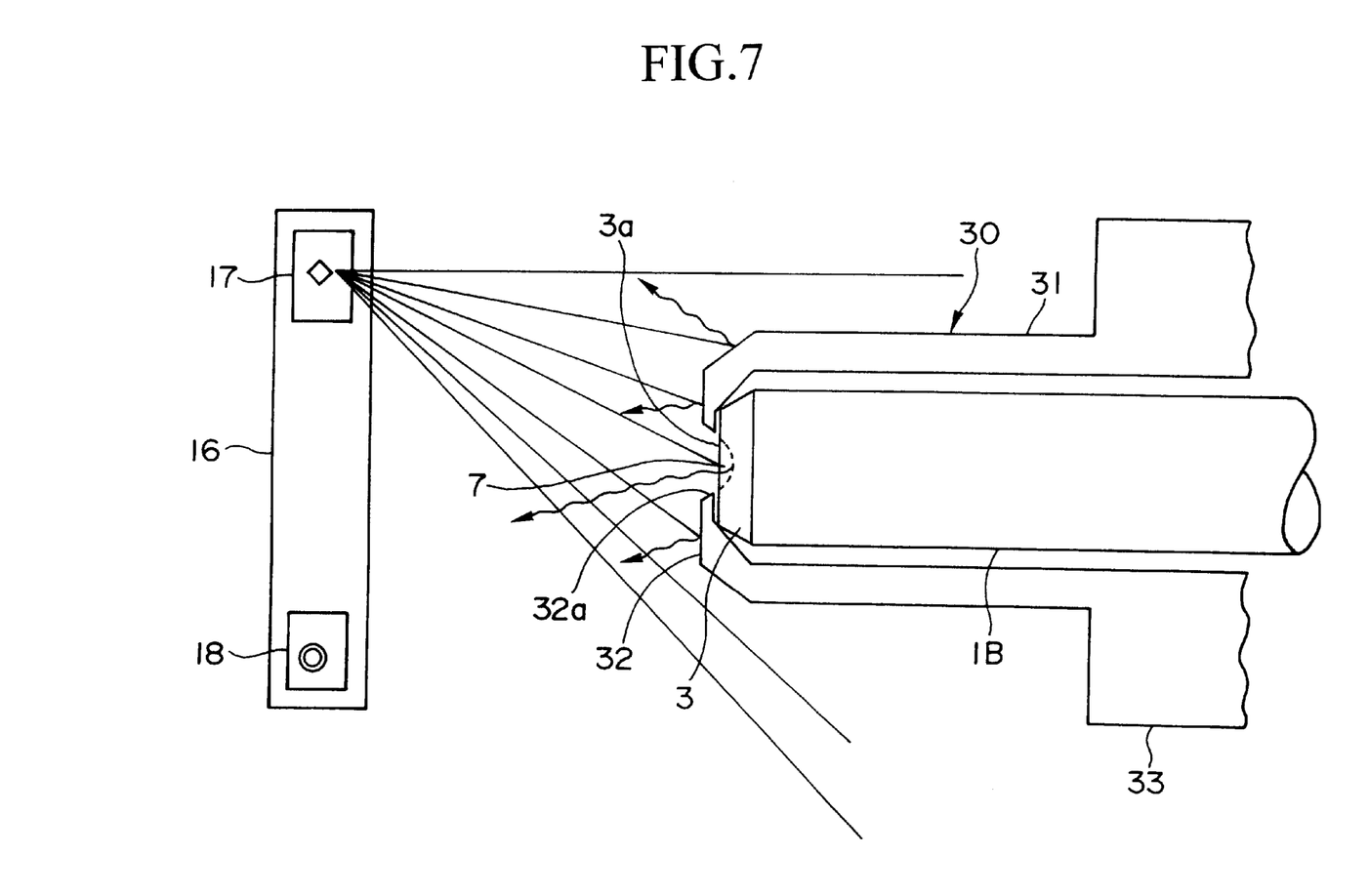
FIG. 7 is a diagram showing a fluorescent X-ray inspection of a fuel rod of another different shape.

FIGS. 6 and 7 are diagrams showing the inspection of fluorescent X-ray radiation in situations where the fuel rod 1 has been substituted for a different variety of fuel rod.

The fuel rod 1A shown in FIG. 6 has a larger external diameter than the fuel rod 1 mentioned above. In this case, the cap 30 is constructed with thinner walls, and when the front end of the fuel rod 1A is covered with the cap 30, the bead portion 7 of the end plug 3 is aligned with the central aperture 32a.

Furthermore, the fuel rod 1B shown in FIG. 7 has a smaller external diameter than the fuel rod 1 of the embodiment of the present invention. In this case, the cap 30 is constructed with thicker walls, and when the front end of the fuel rod 1B is covered with the cap 30, the bead portion 7 of the end plug 3 is aligned with the central aperture 32a.

In the situations shown in FIGS. 6 and 7, the external measurements of both the main body 31 and the front surface 32 of the cap 30 are identical and the internal diameter of the central aperture 32a is also the same, so the amount of fluorescent X-ray radiation generated from the cap 30 during fluorescent X-ray inspection using the X-ray fluorescence inspection apparatus is extremely small, and moreover uniform, meaning the same calibration curve can be used for determining the acceptability of the fuel rod.

In contrast, in the case of fluorescent X-ray inspection employing conventional technology, where no cap is used, differences in the external diameter dimensions of the end surface 3a of the end plug 3 of the fuel rod 1 cause variations in the amount of noise fluorescent X-ray radiation generated therefrom, and so the calibration curve needs to be reset each time, which is complicated.

As described above, with the embodiment of the present invention, by using a covering cap 30 during inspection of the amount of tungsten inclusions, accurate measurements with little noise can be achieved in a short period of time and inspection results of greater precision can be obtained. Moreover, even if the type of fuel rod 1 is altered and there is a change in the external dimensions of the fuel rod, because the external dimensions of the covering cap 30 can be kept the same, the amount of fluorescent X-ray radiation generated from the portion of the cap 30 around the bead portion 7 is extremely small, and moreover does not vary, meaning the same calibration curve can be used for determining the acceptability of the fuel rod.

Furthermore, the titanium cap 30 used in the inspection of the amount of tungsten inclusions in the bead portion 7 is not limited to the configuration described in the present embodiment above, and any suitable configuration can be used which enables the covering of the end surface 3a of the end plug 3 with the exception of the bead portion 7, and which allows a reduction in the amount of fluorescent X-ray radiation generated in the region of the diffraction angle of the spectrum W-Lα.

Figure 8:
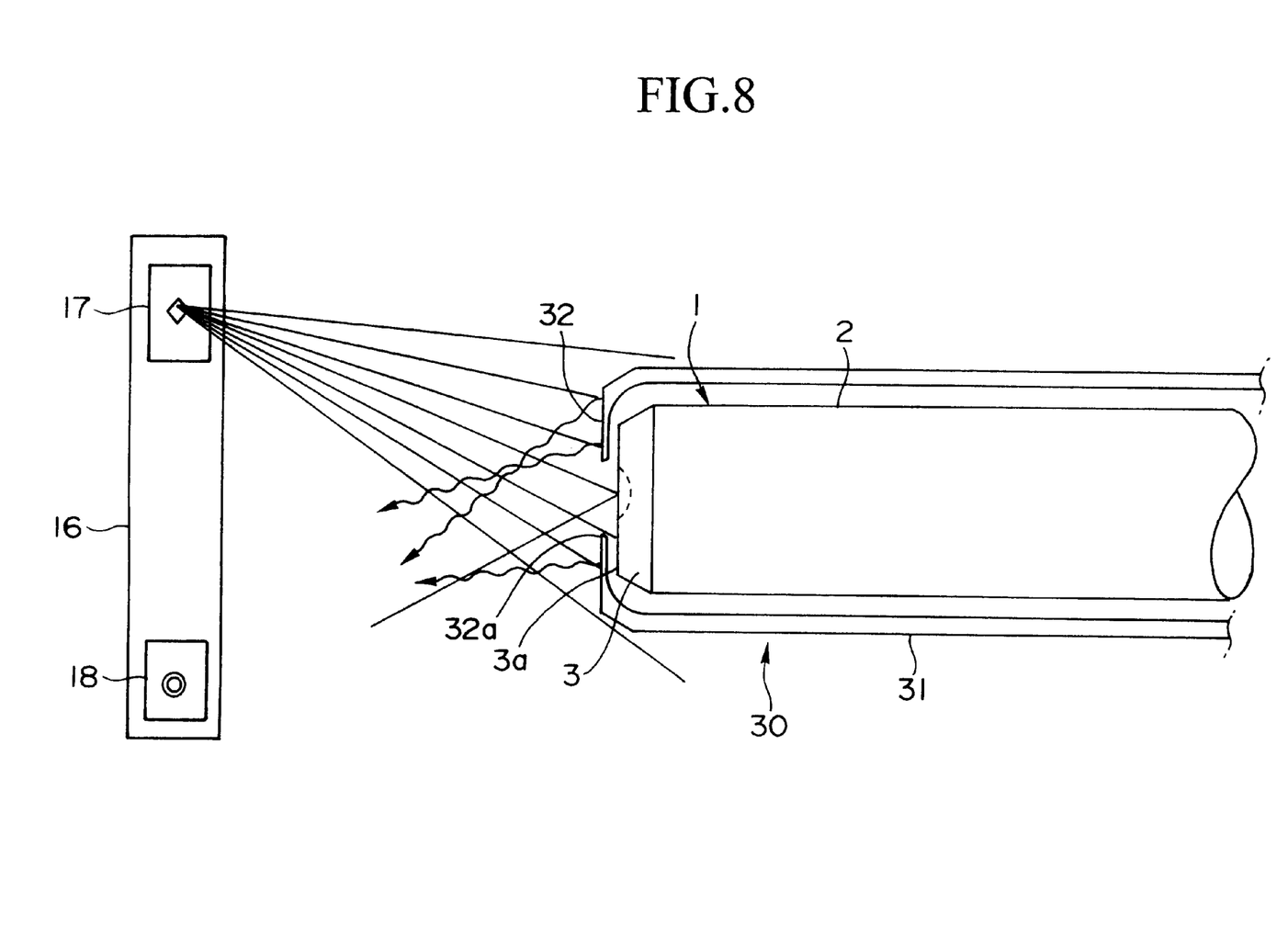
FIG. 8 is a cross-sectional diagram showing a fuel rod covered with a cap of a different shape.

For example, a cap 30 constructed from a main body 31 and a front surface 32, but with no expanded diameter portion 33, as shown in FIG. 8, can also be used. This type of construction can still achieve the desired effects of the present invention, particularly in those cases where the entire spread of the primary X-ray beam emitted by the X-ray fluorescence inspection apparatus falls on the front surface 32a of the cap 30.

Furthermore, the present invention is not limited to the inspection of the amount of tungsten inclusions from a tungsten electrode into the pressure welded portion of the end plug 3 of a fuel rod 1, but can also be used for the fluorescent X-ray inspection of any of the various metals which can be contaminated by tungsten.

The material of the cap 30 is not limited to titanium, and other materials such as iron are suitable, and in principle any metal can be used which has a fluorescent X-ray wavelength different from that of tungsten, and which moreover displays a smaller amount of fluorescent X-ray radiation or a smaller fluorescent X-ray intensity than either the metal of the welded portion or tungsten.

Moreover, the present invention is not limited to the contaminant contained in the welded portion being tungsten, and can be suitably used for all types of metals. In such a case, the metal of the cap which acts as a shielding member should be selected so that at the diffraction angle of the fluorescent X-ray spectrum shown in FIG. 2 corresponding to the contaminant, the fluorescent X-ray wavelength of the selected metal is different from the wavelengths of both the contaminant and the metal of the contaminated welded portion, and moreover the fluorescent X-ray intensity of the metal is comparatively small.

As described above, an X-ray fluorescence inspection apparatus according to the present invention comprises an apparatus wherein the material being inspected comprises a welded portion of a fuel rod which is covered with a shielding member which has an opening corresponding to the position of the welded portion, the shielding member being constructed of a material for which the wavelength of fluorescent X-rays is different from the wavelength of fluorescent X-rays from the contaminant or the material being inspected and for which the intensity of fluorescent X-rays at the diffraction angle of the contaminant is less than the intensity of the fluorescent X-rays from either the contaminant or the material being inspected. When the welded portion is irradiated with primary X-rays through the opening, fluorescent X-rays generated by excitation of the material surrounding the welded portion being inspected will enter the X-ray fluorescence inspection apparatus and appear as noise. However, by covering the area surrounding the welded portion with a shielding member, provided measurements are conducted at the diffraction angle corresponding to the fluorescent X-rays generated by excitation of the contaminant in the welded portion, the amount of fluorescent X-ray radiation resulting from excitation within the shielding member, as measured by the X-ray fluorescence inspection apparatus, will be small and the amount of noise reduced as much as possible. Moreover the amount of fluorescent X-ray radiation resulting from the contaminant will be significantly larger than the amount of noise, enabling an accurate measurement to be conducted in a very short time.

Furthermore, if the shielding member is formed so that the external shape thereof will be the same even if the external dimensions of the covered material being inspected differ, then even if the shape of the material being inspected is altered, because the fluorescent X-ray noise generated by excitation within the area surrounding the opening through which the welded portion is exposed will not only be minimal, but also uniform, the background value arising from noise and the like will not vary. Hence the same calibration curve can be used to determine the acceptability of the material being inspected.

What is claimed is:

1. An X-ray fluorescence inspection apparatus which detects a contaminant in an end plug of a fuel rod, comprising:

an X-ray generator which irradiates the end plug of the fuel rod with primary X-rays;

a fluorescence X-ray detecting device which detects fluorescence X-rays generated from the end plug; and a shielding member which accommodates one end of the fuel rod and has an aperture to expose a portion of the end plug;

wherein the shielding member is constructed of a material for which the wavelength of fluorescent X-rays is different from the wavelength of fluorescent X-rays from the contaminant and the end plug, and for which the intensity of fluorescent X-rays at the diffraction angle of the contaminant is less than the intensity of each of the fluorescent X-rays from both the contaminant and the end plug.

2. The X-ray fluorescence inspection apparatus according to claim 1, wherein the portion to be inspected is a welded portion formed on the center of the end plug, and the shielding member comprises a cylindrical body in which the one end of the fuel rod can be accommodated and a base plate which closes one end of the cylindrical body, and the aperture is formed at the center of the base plate.

3. The X-ray fluorescence inspection apparatus according to claim 1, wherein the shielding member is formed of titanium or iron.

4. The X-ray fluorescence inspection apparatus according to claim 2, further comprising:

a longitudinal positioning device for determining the position of the fuel rod in a longitudinal direction of the fuel rod; and a radial positioning device for determining the position of the fuel rod in a radial direction of the fuel rod.

5. The X-ray fluorescence inspection apparatus according to claim 1, further comprising a plurality of the shielding members for a plurality of samples having external dimensions different from each other, and the shielding members having the same external dimension.

* * * * *